United States Patent
Werding et al.

[11] Patent Number: 6,077,265
[45] Date of Patent: Jun. 20, 2000

[54] NAIL FOR FIXING THE POSITION AND SHAPE OF BROKEN LONG BONES

[76] Inventors: Gerd Werding, Theresienstrasse 29; Willi Schneider, Neuburger Strasse 60, both of D-85049 Ingolstadt, Germany

[21] Appl. No.: 09/389,186

[22] Filed: Sep. 2, 1999

Related U.S. Application Data

[62] Division of application No. 08/954,716, filed as application No. PCT/EP96/01652, Apr. 19, 1996.

[51] Int. Cl.⁷ .................................................. A61B 17/56
[52] U.S. Cl. ................................ 606/67; 606/62; 606/63
[58] Field of Search .................................. 606/62, 63, 60, 606/64, 67, 68; 128/DIG. 20; 600/29, 30, 31; 602/5, 13

[56] References Cited

U.S. PATENT DOCUMENTS

| | | |
|---|---|---|
| 3,426,364 | 2/1969 | Lumb . |
| 4,170,990 | 10/1979 | Baumgart et al. . |
| 4,204,531 | 5/1980 | Aginsky . |
| 4,309,777 | 1/1982 | Patil . |
| 4,349,921 | 9/1982 | Kuntz . |
| 4,446,857 | 5/1984 | Otte et al. .................................. 606/62 |
| 4,554,914 | 11/1985 | Kapp et al. . |
| 4,636,217 | 1/1987 | Ogilvie et al. . |
| 4,686,584 | 8/1987 | Frisch . |
| 4,697,584 | 10/1987 | Haynes . |
| 4,759,769 | 7/1988 | Hedman et al. . |
| 4,854,312 | 8/1989 | Raftopoulos et al. . |
| 5,053,035 | 10/1991 | McLaren .................................. 606/62 |
| 5,102,413 | 4/1992 | Poddar ..................................... 606/62 |
| 5,108,404 | 4/1992 | Scholten et al. . |
| 5,116,335 | 5/1992 | Hannon et al. ........................... 606/62 |
| 5,131,382 | 7/1992 | Meyer . |
| 5,171,278 | 12/1992 | Pisharodi . |
| 5,303,718 | 4/1994 | Krajicek . |
| 5,376,123 | 12/1994 | Klaue et al. . |
| 5,433,718 | 7/1995 | Brinker ..................................... 606/62 |
| 5,480,403 | 1/1996 | Lee et al. . |
| 5,520,690 | 5/1996 | Errico et al. . |
| 5,522,816 | 6/1996 | Dinello et al. . |
| 5,569,249 | 10/1996 | James et al. ............................. 606/62 |
| 5,645,598 | 7/1997 | Brosnahan III . |
| 5,658,287 | 8/1997 | Hofmann et al. . |
| 5,658,310 | 8/1997 | Berger . |
| 5,827,289 | 10/1998 | Reiley et al. . |

FOREIGN PATENT DOCUMENTS

| | | |
|---|---|---|
| 2629337 | 10/1989 | France . |
| 2674119 | 9/1992 | France . |
| 2821785 | 11/1979 | Germany . |
| 1049050 | 10/1983 | U.S.S.R. . |
| 2114005 | 8/1983 | United Kingdom . |
| 2268068 | 1/1994 | United Kingdom . |
| WO 90/00037 | 1/1990 | WIPO . |
| WO 92/14423 | 9/1992 | WIPO . |
| WO 96/11643 | 4/1996 | WIPO . |
| WO 93/37170 | 11/1996 | WIPO . |

*Primary Examiner*—Gene Mancene
*Assistant Examiner*—Pedro Philogene
*Attorney, Agent, or Firm*—Levisohn, Lerner, Berger & Langsam

[57] ABSTRACT

A nail for fixing the position and shape of broken long bones is provided. The nail has a longitudinal shank defining a central main body and longitudinal extending, radially directed, ribs, preferably one or more. The nail and ribs are collapsed in diameter when inserted into the broken bone and then, by introducing a fluid into the hollow nail, the diameter of the nail increases such that the rib(s) contact the interior of the broken bone.

14 Claims, 9 Drawing Sheets

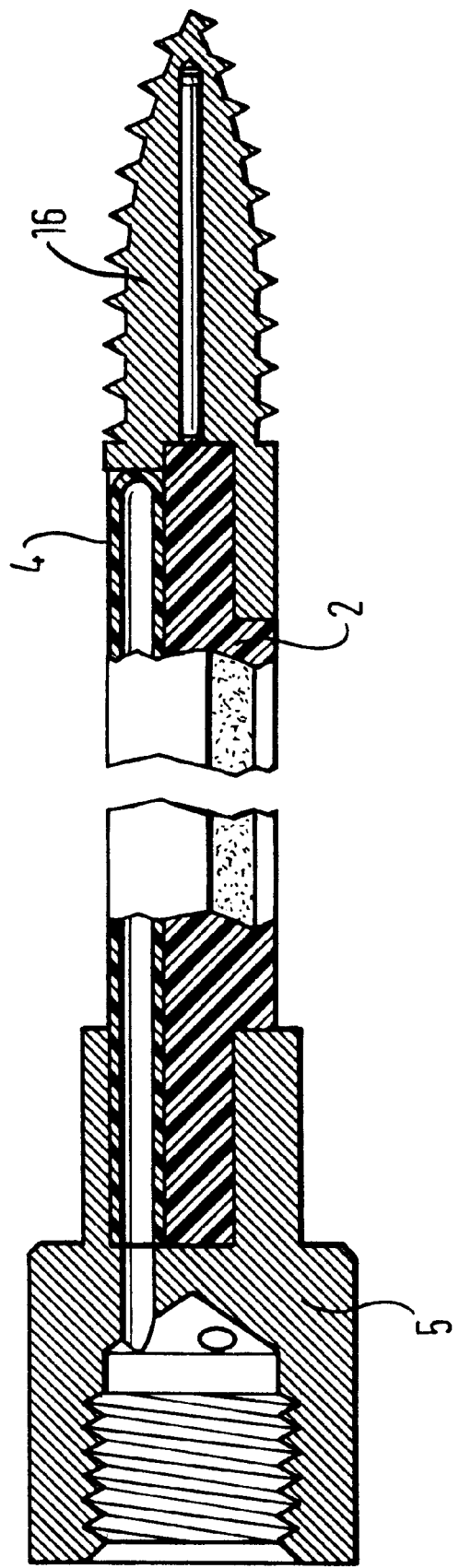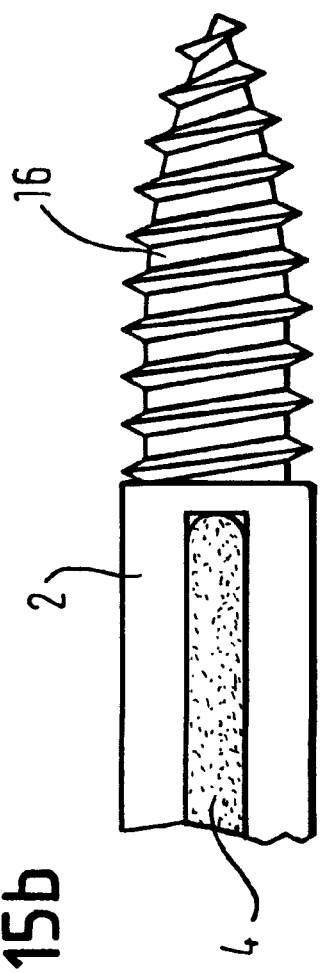
Fig. 15a
Fig. 15b

NAIL FOR FIXING THE POSITION AND SHAPE OF BROKEN LONG BONES

RELATED APPLICATIONS

This application is a divisional of U.S. application Ser. No. 08/954,716 filed Oct. 20, 1997 pending which is a National Phase filing under 35 USC Section 371 of PCT/EP96/01652 filed Apr. 19, 1996 which claims priority upon German application 195 14 758.8, filed Apr. 21, 1995. Applicant claims all rights of priority to these applications.

BACKGROUND OF THE INVENTION

1. Field of the Invention

The invention relates to a nail for fixing the position and shape of broken long bones.

2. Description of the Related Art

Up until now, relatively large steel nails having a predominantly U-shaped or V-shaped cross section have been used for internally stabilizing broken long bones. The nails stabilize the bones according to the principle of providing support at three points, namely at the beginning, at the end and in the mid-section of the nail. In order to position such nails, large passages matching the diameter of the implanted nail must be cut through the surface of the bone and then through the medullary cavity of the bone. This has the disadvantage that almost all of the medullary cavity has to be reamed out in order to produce such a passage, and as a result in particular the blood supply of the bone is impaired. In addition, because of the three-point support, the force is transmitted via a relatively small area, and to ensure rotational stability it is necessary to use additional mechanisms such as locking screws and the like.

Removing the intramedullary nail after the bone has healed is also a procedure requiring a relatively high degree of effort. The nail is wedged in the medullary cavity and must be knocked out of the cavity using special tools and applying a relatively large amount of force. Again, considerable damage may be sustained by the medullary cavity in the process.

From DE-C-32 01 056 an intramedullary nail is known, in which the shank consists of a hollow body made of a memory alloy which can assume two possible shapes, as a function of temperature. Thus, when in situ, the intramedullary nail can be transformed from having a small cross section to having an expanded cross section, and vice versa. The disadvantage of this prior art type of intramedullary nail is that the application of heat required to expand the diameter of the shank of the nail also causes thermal stress in the bone and the bone marrow.

A nail according to the preamble of claim 1 is known from U.S. Pat. No. 5,102,413. In this known nail a single expandable bladder surrounds fully the main body of the nail.

SUMMARY OF THE INVENTION

An object of the invention is to create a nail for fixing the position and shape of the broken long bones which provides good stabilization and can be implanted without causing large-scale damage to the medullary cavity, and which also does not place any thermal stress at all on the bone and bone marrow.

The object is solved according to the invention by means of a nail having a shank including a central main body and longitudinal chamber-like expansion elements attached to the central main body which are expandable while in situ.

The expansion elements run substantially the entire length of the shank and are arranged substantially equiangularly around the central main body. When the expansion elements are expanded, a cross-section of the central main body is expanded.

According to the present invention, the nail in the non-expanded state, i.e. while it still has a small diameter, can be inserted through a relatively small cortical channel into the medullary cavity. It is not necessary to ream out the medullary cavity, thereby damaging large sections of it. When the nail is fully implanted, its cross section is expanded without the application of heat, to the extent required in order to stabilize the broken bone. The supporting forces are then distributed over a large area. Rotational stability is also achieved through the surface contact and the resulting adaptation to the given shape of the medullary cavity.

Since the cross sectional enlargement is reversible, as described in Claim 2, the implant may be removed in a manner that is particularly protective of the tissue, once the bone has healed.

Further advantageous embodiments of the invention are the subject of the other sub-claims.

BRIEF DESCRIPTION OF THE DRAWINGS

Preferred embodiments of the invention will now be described on the basis of the attached drawings, which show:

FIGS. 15a and 15b an embodiment of a nail according to the invention seen in longitudinal section and partial lateral view, respectively, with a screw tip.

DETAILED DESCRIPTION OF THE PREFERRED EMBODIMENTS

Figure 1:
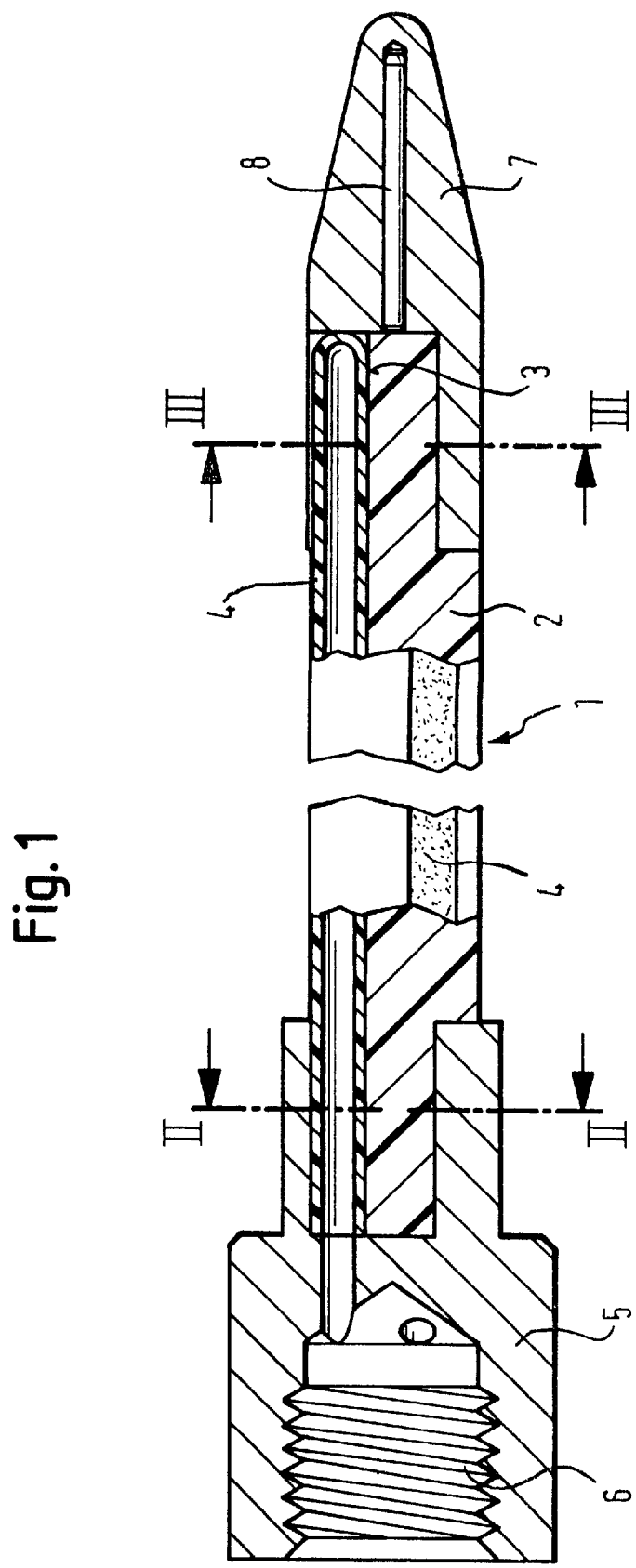
FIG. 1 an embodiment of the nail according to the invention, seen her in longitudinal section.
Figure 3:
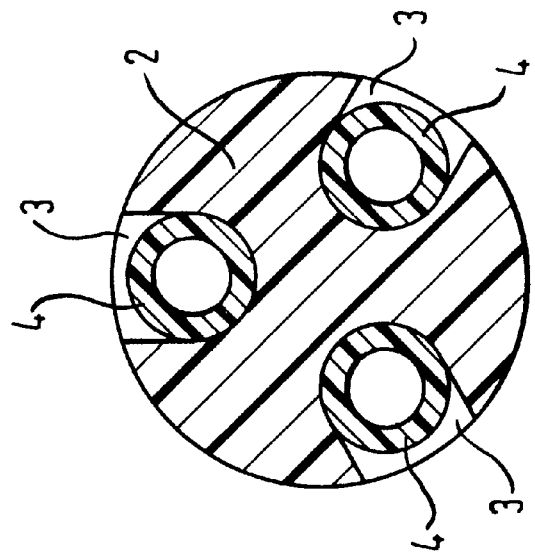
FIG. 3 a cross section along the line A—A in FIG. 1.
Figure 2:
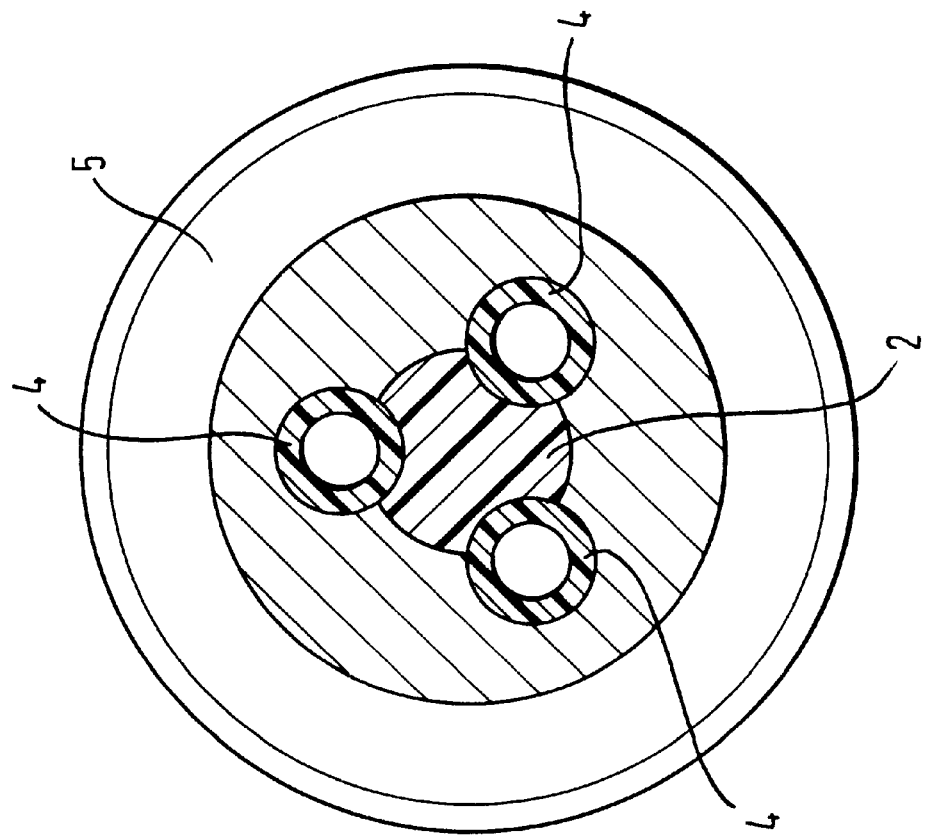
FIG. 2 a cross section along the line B—B in FIG. 1.
Figure 10:
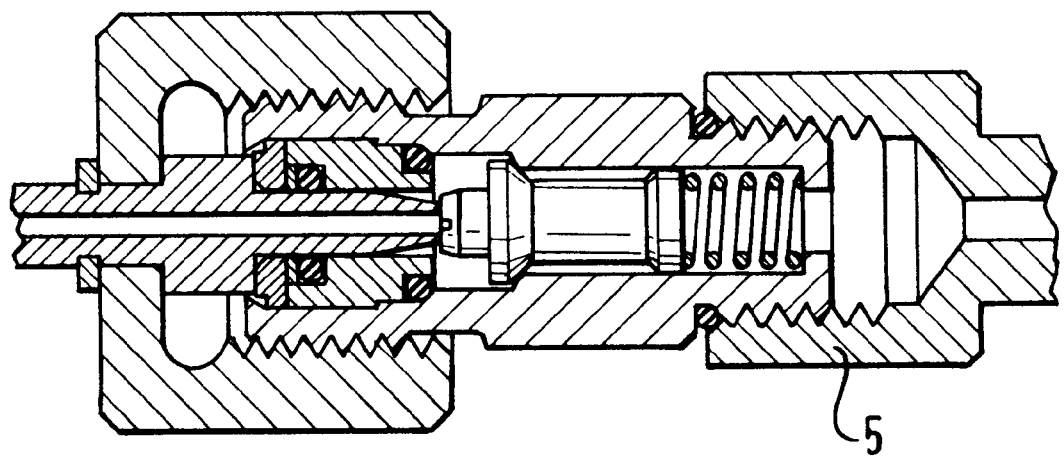
FIG. 10 an embodiment of a valve, seen in longitudinal section, used in the head of the nail shown in FIG. 1.

The nail for long bones, as illustrated in FIG. 1, possesses a shank 1 having a main section 2 made preferably of tissue-compatible plastic. This main section 2 is essentially dimensionally stable, but preferably possesses a certain amount of flexural elasticity. In the embodiment shown here it is circular in cross section and is provided with three grooves 3 (See FIG. 3) running longitudinally and arranged at intervals of 120° around the periphery. In these grooves are mounted tubular expansion elements 4, also preferably made of tissue-compatible plastic, which are preferably elastically expandable in cross section. In the unpressurized resting state, the expansion elements 4 preferably do not extend beyond the outer contour of the main section 2. The head 5 of the nail is formed as the connector for a filling and discharging valve, as shown in FIG. 10, and it is provided with a corresponding connecting thread 6 for the valve. At the tip of the nail is located an end cap 7 which is preferably conically shaped to facilitate insertion of the nail. The tip contains preferably a metal pin 8 which is visible under X-ray monitoring, thus facilitating the insertion of the nail. It is also conceivable to use a metal strip extending over the entire length of the nail.

Figure 4:
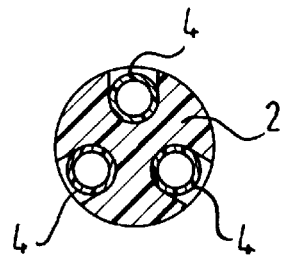
FIG. 4 another cross section along line A—A with the expansion elements retracted and expanded.
Figure 4:
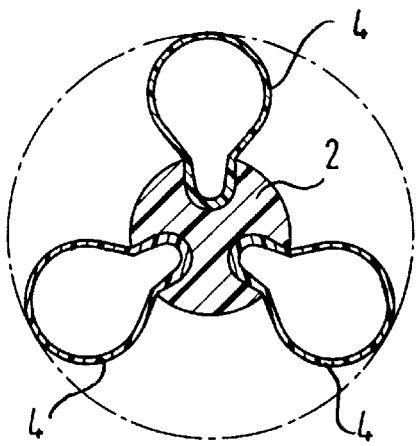
Figure 7:
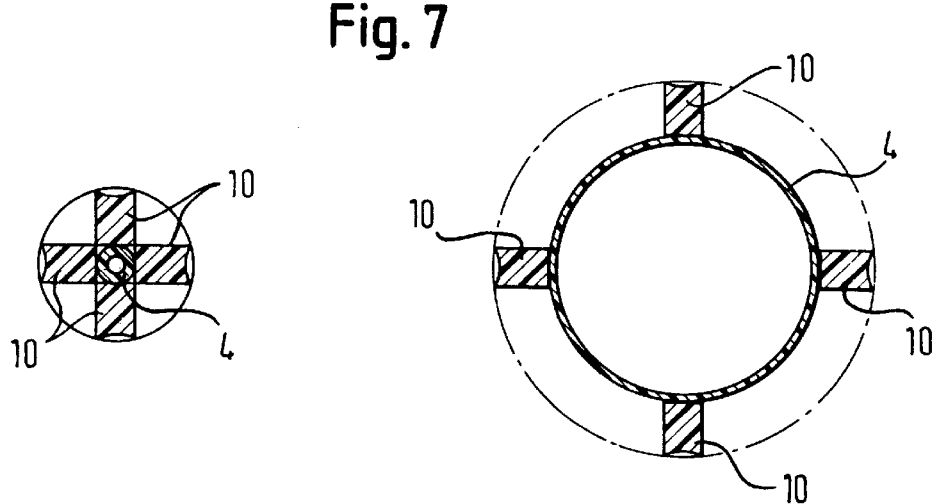
FIGS. 7–9 are a cross-sectional views of other embodiments of the main section of the shank and the expansion elements in retracted and expanded states.
Figure 8:
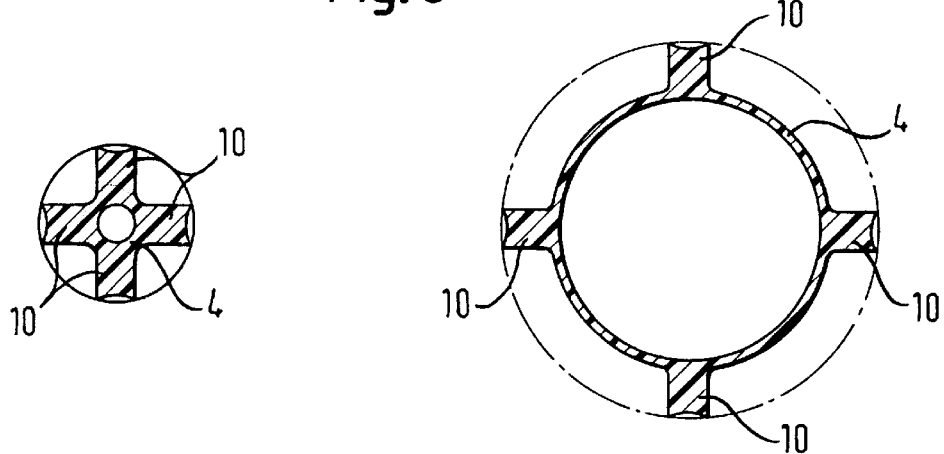
Figure 9:
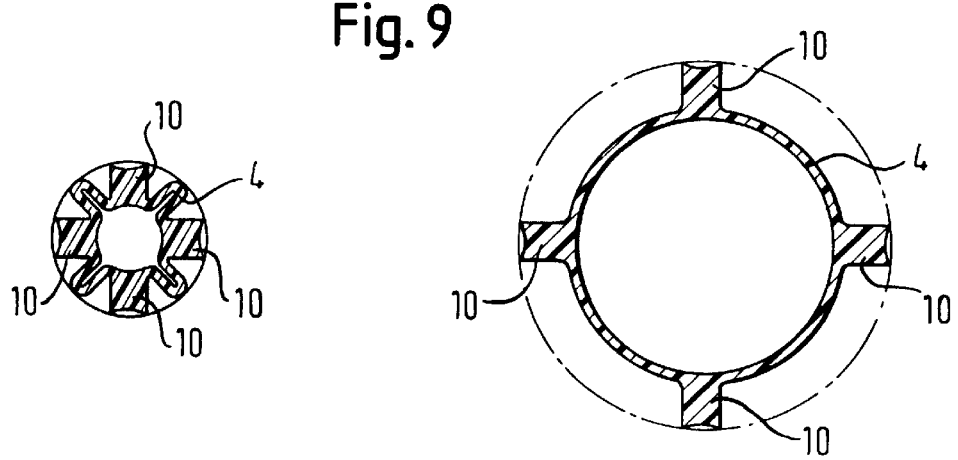

When the expansion elements 4, each of which has the form of a chamber, are pressurized internally by pumping in a gas or a fluid—physiological saline solution is ideal from the medical standpoint—they expand as shown in FIG. 4, so that the cross section of the shank 1 of the nail is enlarged overall. An approximately star-shaped structure when seen in cross sectional view is formed. The parts extending farthest outwards fill only a fraction of the circumscribed cross section, so that sufficient space is left into which the bone marrow can be displaced. The type and size of the contact area with the bone can be influenced by appropriately shaping the cross section of the expansion elements as shown in FIGS. 7–9, for example. The flexural elasticity of the main section 2, and thus of the shank 1 in general, allows the shank also to follow curvatures in the medullary cavity and, together with the nature of the expansion elements, ensure uniform contact with the bone in a lengthwise direction.

Figure 5:
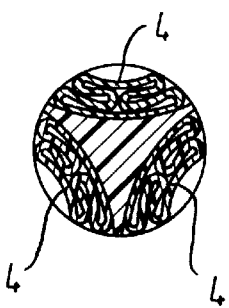
FIG. 5 a cross section, corresponding to that in FIG. 4, of another embodiment of the main section of the shank and of the expansion elements.
Figure 5:
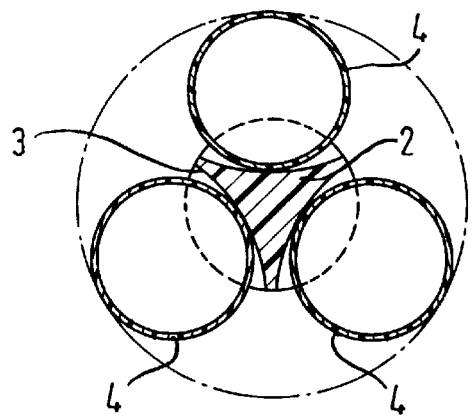

FIG. 5 shows an embodiment in which the chamber-like expansion elements have the form not of elastic elements but of folded elements which lie in the, in this case, concave grooves 3 when not pressurized.

Figure 6:
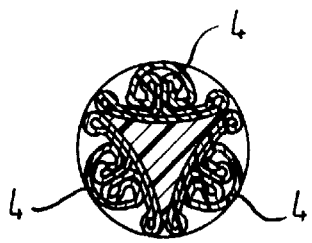
FIG. 6 a cross section, corresponding to that in FIG. 4, of another embodiment of the main section of the shank and of the expansion elements.
Figure 6:
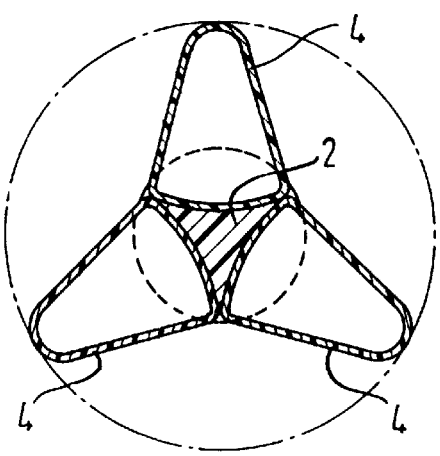

FIG. 6 shows an embodiment in which expansion elements are folded when they are not pressurized and expand to form shapes of triangular cross section with rounded tips.

FIGS. 7–9 depict embodiments of the nail shank 1 in which a central main section of the kind referred to above is not present. Instead, the central element is formed by an expandable or, in the unpressurized state, a folded, tubular expansion element 4 around the periphery of which, and integrally formed therewith or attached thereto, are arranged ribs 10 extending axially and projecting radially, the ribs 10 being dimensionally stable and having a desired amount of flexural elasticity. When the expansion element is unpressurized, the ribs 10 are arranged close together and define a shank of small cross section. When the expansion element 4 is inflated with gas or liquid, in particular with physiological saline solution, the cross-sectionally enlarged expansion element 4 defines the cross section of the shank of the nail, and attached ribs 10, which are the elements in contact with the bone, continue to provide the stiffness of the nail shank.

Figure 11:
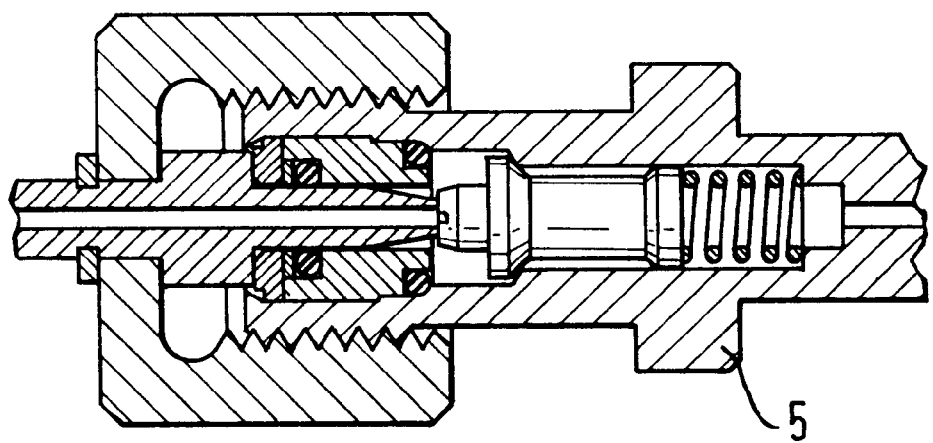
FIG. 11 a view, corresponding to that in FIG. 7, of an embodiment in which the head of the nail is designed as part of the valve.
Figure 12:
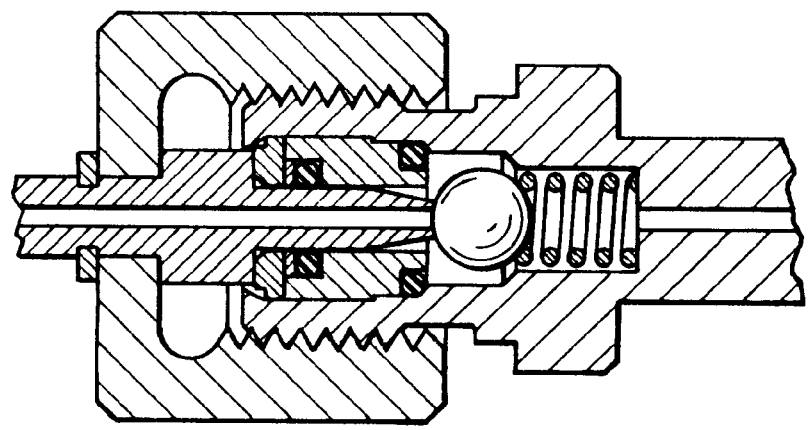
FIG. 12 an embodiment similar to that in FIG. 11, having a sphere instead of a piston as the sealing body.

In order to expand the nail shank, for example, a valve fitted in the head 5 of the nail is used, as shown in FIG. 10. In the embodiments illustrated in FIGS. 11 and 12, the nail head 5 is designed in such a manner that it is itself part of the valve. The same valve is also used to release the pressure in the expansion element or elements 4, i.e. to discharge the expansion medium with which said element or elements have been filled.

Figure 13:
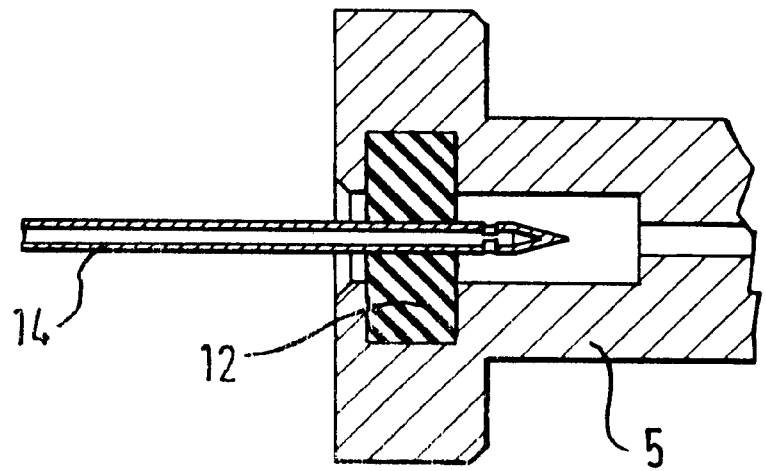
FIG. 13 an embodiment having a perforable membrane instead of the valve.

In an especially advantageous embodiment of the invention, as illustrated in FIG. 13, the nail head 5 contains merely a perforable membrane 12 for a canula 14 by means of which a liquid can be pumped in to fill the expansion elements. Once they have been expanded, the canula 14 is withdrawn and the perforable membrane 12 seals itself automatically. To drain off the expansion liquid once the healing process is complete, the canula is again inserted trough the membrane and the liquid is drawn off once more.

Figure 14:
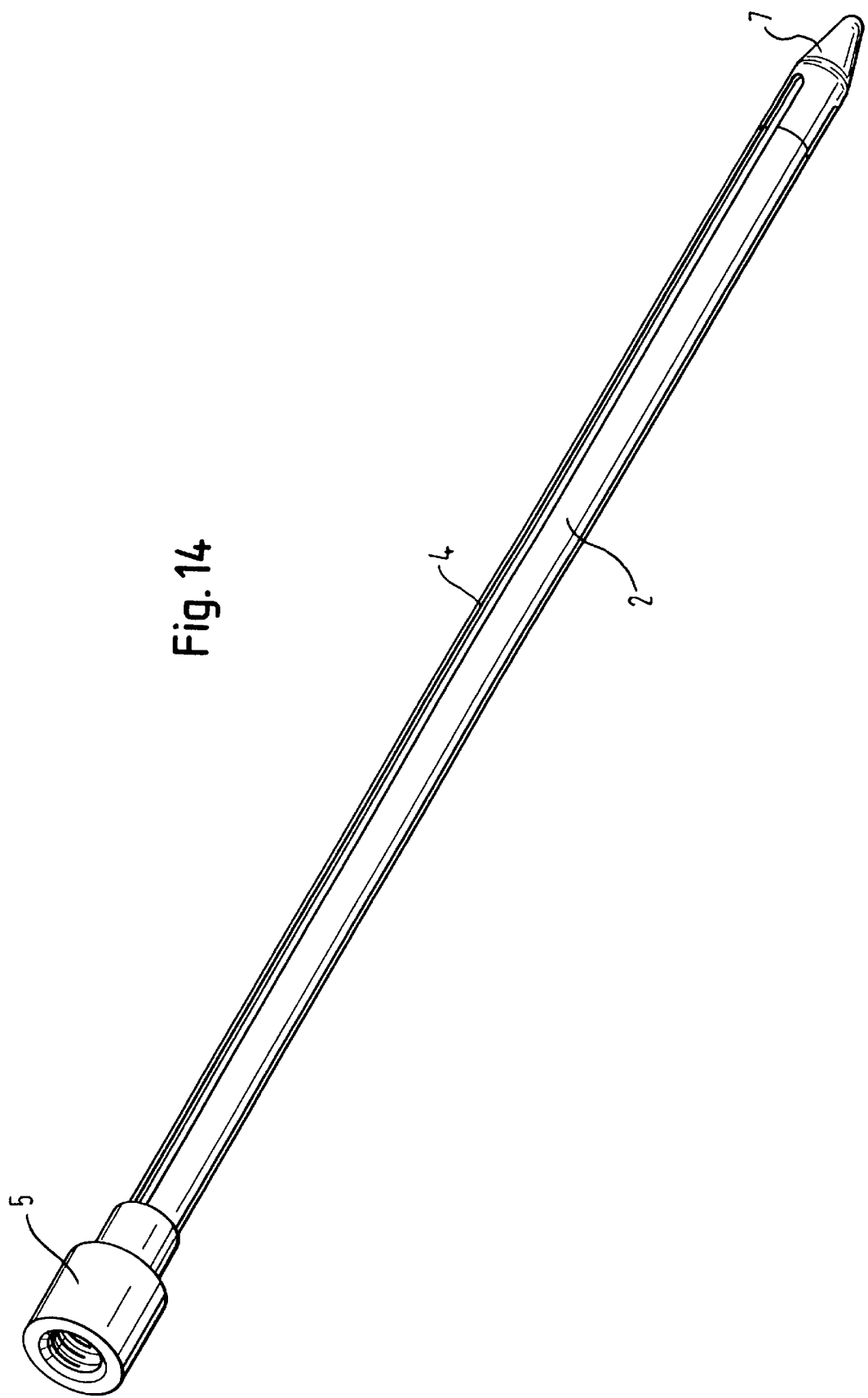
FIG. 14 a diagonal perspective view of the nail from FIG. 1.

FIG. 14 shows a diagonal perspective view of the nail which is seen in longitudinal section FIG. 1. The nail has a typical length of between 25 and 35 cm corresponding to the length of the femur.

Figure 16A:
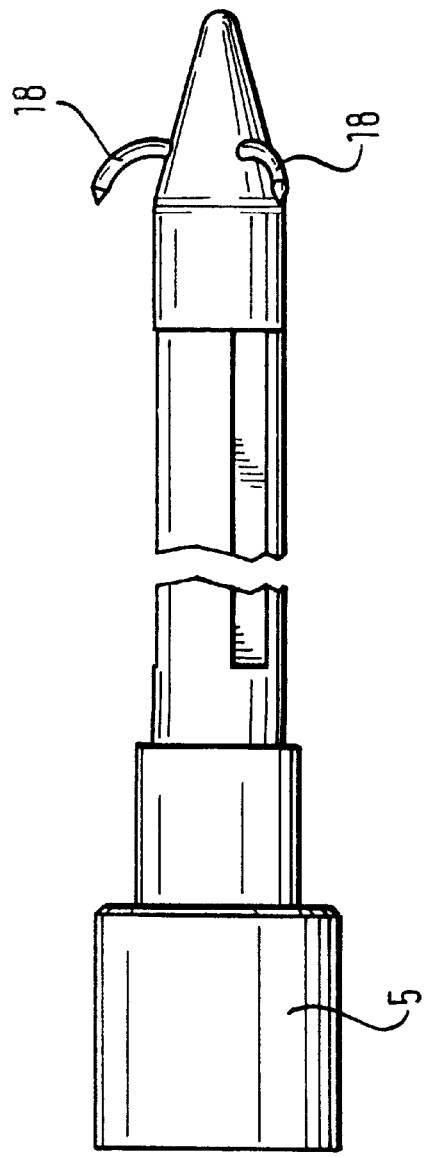
FIGS. 16a and 16b a lateral view and a front view, seen from the tip, of a nail having extendable elements in the tip.
Figure 16B:
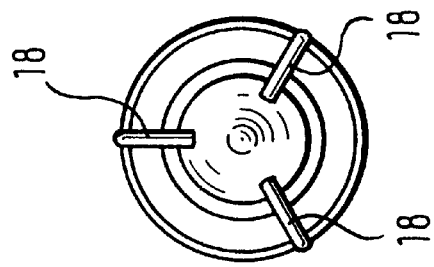

FIGS. 15*a* and 15*b* show an embodiment of the nail having a threaded tip 16 which permits special anchoring of the nail in the bone, as do also the strut arrangement 18 shown in the embodiment illustrated in FIGS. 16*a* and 16*b*.

In a preferred design, the nail is made from a material that can be resorbed by the body. This makes it unnecessary to remove the nail once healing is complete.

What is claimed is:

1. A nail for fixing the position and shape of broken long bones, said nail possessing a shank (1) having a central main section (2) and possessing a chamber-type expansion element (4) attached to and extending over the length of the main section, and said expansion element can be internally pressurized in situ and caused to expand radially by means of a gas or liquid, characterized in that several expansion elements (4) are arranged around and extend over the length of the main section (2).

2. A nail for fixing the position and shape of broken long bones, said nail comprising:

a hollow body comprising a chamber section with a longitudinal axis, said chamber section being inflatable and expandable in cross section along said longitudinal axis, said body further comprising at least one rib extending along said longitudinal axis, said rib(s) extending radially outward from said body, said body having a reduced in diameter cross section when initially inserted into the broken bone of a patient and an enlarged in diameter cross section when inflated by the introduction of fluid into said chamber section.

3. A nail as claimed in claim 2 wherein said body is basically cylindrical.

4. A nail as claimed in claim 2 wherein said body is formed from tissue compatible plastic.

5. A nail as claimed in claim 2 wherein said body has three or more equiangularly spaced ribs.

6. A nail as claimed in claim 5 wherein said body is provided with four ribs.

7. A nail as claimed in claim 2 wherein at least two ribs are provided.

8. A nail as claimed in claim 7 wherein radial spacing between said ribs on said body is formed by web portions of the outside wall of said hollow body.

9. A nail as claimed in claim 2 wherein said body expands substantially uniformly along said longitudinal axis.

10. A nail as claimed in claim 2 wherein said enlarged in diameter cross section of said body is a result of the reduction in thickness of said hollow body from its reduced in diameter cross section.

11. A nail as claimed in claim 2 wherein said enlarged in diameter cross section of said hollow body is a result of the unfolding of the hollow body segments between said ribs.

12. A nail as claimed in claim 2 wherein said body, in said reduced in diameter cross section, defines at least a pair of folded-upon themselves wall segments separated by said rib(s).

13. A nail as claimed in claim 2 wherein said reduced in diameter cross section is defined by the outside edges of said rib(s).

14. A nail as claimed in claim 2 wherein two or more ribs are provided on said wall of said body and the web portion of said wall, defined as the spacing of the wall between said ribs, is folded while said body is in its reduced in diameter cross section.

* * * * *